United States Patent
Iskander et al.

(10) Patent No.: US 9,526,438 B2
(45) Date of Patent: Dec. 27, 2016

(54) MICROWAVE STETHOSCOPE FOR MEASURING CARDIO-PULMONARY VITAL SIGNS AND LUNG WATER CONTENT

(71) Applicants: Magdy F. Iskander, Honolulu, HI (US); Nuri Celik, Honolulu, HI (US); Ruthsenne Gagarin, Pearl City, HI (US); Gui Chao Huang, Honolulu, HI (US); Darcy Alan Bibb, Honolulu, HI (US)

(72) Inventors: Magdy F. Iskander, Honolulu, HI (US); Nuri Celik, Honolulu, HI (US); Ruthsenne Gagarin, Pearl City, HI (US); Gui Chao Huang, Honolulu, HI (US); Darcy Alan Bibb, Honolulu, HI (US)

(73) Assignee: University of Hawaii, Honolulu, HI (US)

( * ) Notice: Subject to any disclaimer, the term of this patent is extended or adjusted under 35 U.S.C. 154(b) by 128 days.

(21) Appl. No.: 14/261,884

(22) Filed: Apr. 25, 2014

(65) Prior Publication Data

US 2014/0323823 A1    Oct. 30, 2014

Related U.S. Application Data

(60) Provisional application No. 61/816,632, filed on Apr. 26, 2013, provisional application No. 61/932,958, filed on Jan. 29, 2014.

(51) Int. Cl.
*A61B 5/00* (2006.01)
*A61B 5/05* (2006.01)
(Continued)

(52) U.S. Cl.
CPC .......... *A61B 5/0507* (2013.01); *A61B 5/0205* (2013.01); *A61B 5/02444* (2013.01);
(Continued)

(58) Field of Classification Search
None
See application file for complete search history.

(56) References Cited

U.S. PATENT DOCUMENTS

| 4,240,445 A | 12/1980 | Iskander | |
| 4,488,559 A * | 12/1984 | Iskander | A61B 5/05 600/430 |

(Continued)

FOREIGN PATENT DOCUMENTS

CN    85107022    9/1985

OTHER PUBLICATIONS

Yuehui Ouyang and William J. Chappell, "High Frequency Properties of Electro-Textiles for Wearable Antenna Applications", IEEE Transactions on Antennas and Propagation, 56:2, 2008.*

(Continued)

*Primary Examiner* — Tse Chen
*Assistant Examiner* — Joanne Hoffman
(74) *Attorney, Agent, or Firm* — Leighton K. Chong

(57) ABSTRACT

A microwave stethoscope measurement method and sensor design employ a microwave transmission sensor and a microwave reception sensor placed on a patient's chest in spaced-apart side-by-side configuration for monitoring patient vital signs, lung water content and other critical measurements. The side-by-side sensors are spaced apart a separation distance of about 1-3 cm in lateral chest orientation. The sensors may be formed with a textile fabric for wearer comfort and to improve contact with the patient's skin. The microwave sensor measurements are digitally processed using a modified short time Fourier Transform (STFT) spectrum windowed-averaged algorithm. Output data extracted from the microwave sensor measurements (Continued)

may be transmitted wirelessly to a mobile device such as a smartphone for remote monitoring of the patient's medical condition.

20 Claims, 14 Drawing Sheets

(51) Int. Cl.
*A61B 5/0205* (2006.01)
*A61B 5/024* (2006.01)
*A61B 5/08* (2006.01)

(52) U.S. Cl.
CPC .......... *A61B 5/0816* (2013.01); *A61B 5/4878* (2013.01); *A61B 5/6804* (2013.01); *A61B 2562/125* (2013.01)

(56) References Cited

U.S. PATENT DOCUMENTS

| | | | |
|---|---|---|---|
| 4,510,437 A | 4/1985 | Iskander | |
| 5,045,862 A * | 9/1991 | Alden | H01Q 1/248 343/700 MS |
| 5,749,369 A * | 5/1998 | Rabinovich | A61B 5/0535 600/372 |
| 7,149,576 B1 * | 12/2006 | Baura | A61B 5/02028 607/6 |
| 7,811,234 B2 | 10/2010 | McGrath | |
| 2005/0235482 A1 * | 10/2005 | Deaett | H01P 11/00 29/600 |
| 2006/0220961 A1 * | 10/2006 | Tinsley | H01Q 9/045 343/700 MS |
| 2006/0247505 A1 * | 11/2006 | Siddiqui | A61B 5/0024 600/300 |
| 2006/0259027 A1 * | 11/2006 | Kwan | A61B 18/1477 606/41 |
| 2010/0256462 A1 * | 10/2010 | Rappaport | A61B 5/00 600/301 |
| 2011/0130800 A1 | 6/2011 | Weinstein | |
| 2011/0306859 A1 * | 12/2011 | Saldivar | A61B 5/6823 600/365 |

OTHER PUBLICATIONS

Nuri Celik, Ruthsenne Gagarin, Hyong-sun Youn, and Magdy F. Iskander, "A Noninvasice Microwave Sensor and Signal Processing Technique for Continuous Monitoring of Vital Signs", IEEE Antennas and Wireless Propagation Letters, 10, 2011.*
C. Staub, "Measurement of Lung Water Content," Journal of Microwave Power, vol. 18, No. 3, pp. 259-263, 1983.
Nagae, D; Mase, A., "Measurement of heart rate variability and stress evaluation . . .", Review of Scientific Instruments, vol. 81, Issue: 9.
Nowak, K; Gross, W; Nicksch, K, "Intraoperative lung edema monitoring by microwave reflectometry." Interactive cardiovascular and thoracic surgery [1569-9293] 2011, vol. 12 iss:4 p. 540-544.
Serra, A, "A Single on—Body Antenna as a Sensor for Cardiopulmonary Monitoring," IEEE Antennas and Wireless Propagation Letters [1536-1225] 2010, vol. 9 p. 930-933.
Zhang, Lanlin; Wang, Zheyu; Volakis, J.L., "Textile Antennas and Sensors for Body—Worn Applications," Antennas and Wireless Propagation Letters, IEEE 2012, p. 1690-1693.
Sun, JX; Reisner, AT; Mark, RG, "A signal abnormality index for arterial blood pressure waveforms," Computers in Cardiology, 2006.

Li, B.N.; Dong, M.G.; Vai, M., "On an automatic delineator for arterial blood pressure waveforms," Biomedical Signal Processing and Control, vol. 5, Issue 1, Jan. 2010, pp. 76-81.
Mundt, C.W., et al, "A multiparameter wearable physiologic monitoring system for space and terrestrial applications," IEEE Trans. Inf. Technol. Biomed., vol. 9 (3) (2005), pp. 382-391.
Paradiso, R; Loriga, G; Taccini, N, "A Wearable Health Care System Based on Knitted Integrated Sensors," IEEE Transactions on Information Technology in Biomedicine, v9, No. 3, Sep. 2005.
Pacelli, M; Loriga., G; Taccini, N; Paradiso, R, "Sensing Fabrics for Monitoring Physiological and Biomechanical Variables: E—textile Solutions," Proceedings of the 3rd IEEE—EMBS International Summer School and Symposium on Medical Devices and Biosensors, MIT, Boston, USA, Sep. 4-6, 2006.
Heilman, KJ; Porges, S.W., "Accuracy of the Lifeshirt (Vivometrics) in the Detection of Cardiac Rhythms," Biol. Psychol., vol. 3, pp. 300-3005, 2007.
Pandian, PS; K. Mohanavelu, K; Safeer, KP; Kotresh, TM; Shakunthala, DT; Gopal, P, Padaki, VC, "Smart Vest: Wearable multi-parameter remote physiological monitoring system," Medical Engineering and Physics, May 1, 2008, vol. 30, Issue 4, pp. 466-477.
Haahr, RG; Duun, S; Thomsen, EV, "A wearable "electronic patch" for wireless continuous monitoring of chronically diseased patients," Proceedings of the 5th International Workshop on Wearable and Implantable Body Sensor Networks, 2008.
Zhang, ZB; Shen, YH; Wang, WD, "Design and implementation of sensing shirt for ambulatory cardiopulmonary monitoring," Journal of Medical and Biological Engineering, 31(3): 207-216, 2010.
Di Rienzo, M.; Rizzo, F.; Parati, G ; Brambilla, G.; Ferratini, M.; Castiglioni, P., "MagIC System: a New Textile-Based Wearable Device for Biological Signal Monitoring. Applicability in Daily Life and Clinical Setting," 2005 IEEE Engineering in Medicine and Biology 27th Annual Conference 2005, p. 7167-7169.
Johnstone, JA; Ford, PA; Hughes, G, "Reliability and Validity of the Zephyr™ BioHarness™ to Measure Respiratory Responses to Exercise," Measurement in Physical Education and Exercise Science [1091-367X] 2011, vol. 15 iss:4, p. 293-300.
Iskander, MF; Dumey, CH; Shoff, DJ; Bragg, DG, "Diagnosis of pulmonary edema by a surgically non-invasive microwave technique," Radio Science, vol. 14, pp. 265-269, 1979.
Iskander, MF; Dumey, C; Bragg, D; Ovard, B, "A microwave method for estimating absolute value of average lung water," Radio Science, vol. 17, p. 111, 1982.
Iskander, MF; Dumey, CH, "Microwave Methods of Measuring Changes in Lung Water," Journal of Microwave Power, vol. 18, pp. 265-275, 1983.
Celik, N; Gagarin, R; Youn, HS; Baker, J; Iskander, MF, "On the development of a low-cost real-time remote patient monitoring system using a novel non-invasive microwave vital signs sensor," in IEEE ICWIT Conference, Honolulu, 2010.
Gagarin, R.; Celik, N.; Youn, HS; Iskander, MF, "Microwave Stethoscope: a new method for measuring human vital signs," Antennas and Propagation (APS-URSI International Conference), IEEE International Symposium, Jul. 2011.
Celik, N; Gagarin, R; Youn, HS; Iskander, MF, "A Non-Invasive microwave sensor and signal processing technique for continuous monitoring of vital signs," IEEE Antennas and Wireless Propagation Letters, vol. 10, pp. 286-289, Feb. 2011.
Gagarin, R; Youn, HS; Celik, N; Iskander, MF, "Noninvasive microwave technique for hemodynamic assessments," 2010 APS-URSI International Conference, Toronto, Canada, Jul. 2010.
Madsen, AH, et al, "Signal processing methods for Doppler radar heart rate monitoring," in Signal Processing Techniques for Knowledge Extraction and Information Fusion, D. Mandic, M. Golz, ed., Springer, 2008.

* cited by examiner

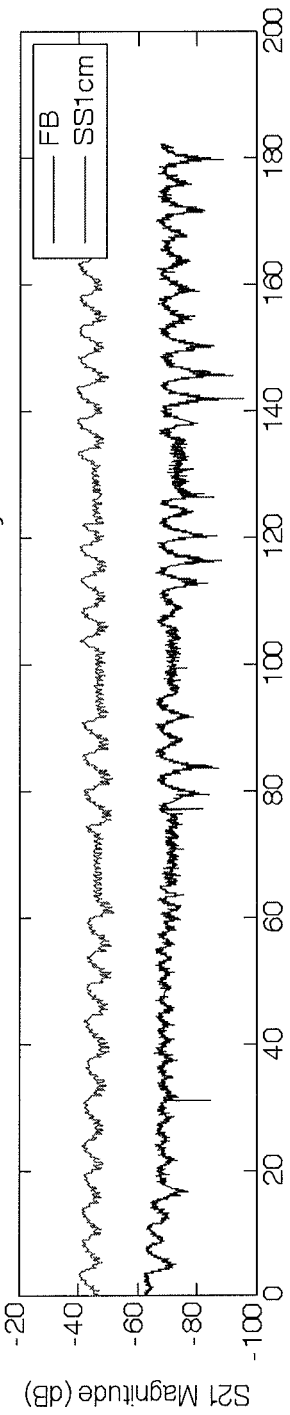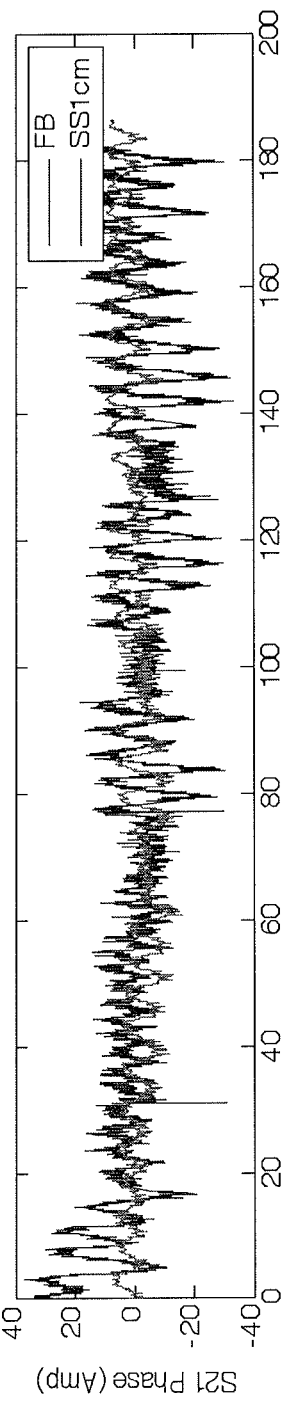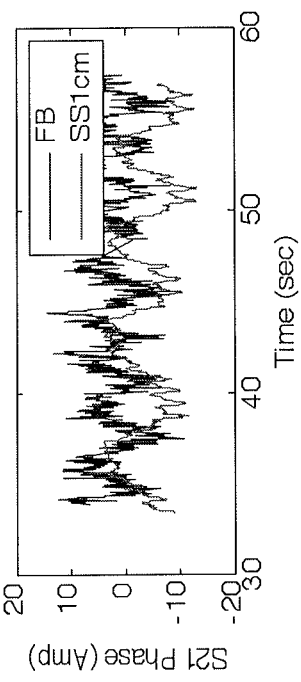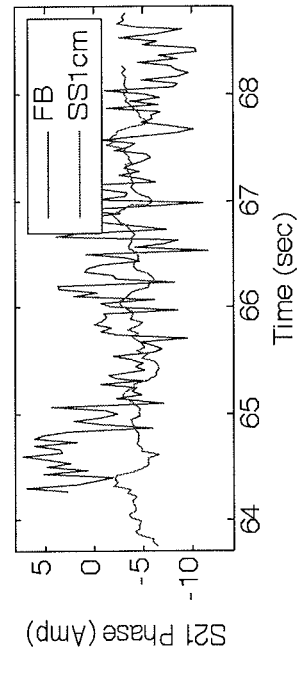
FIG. 8A
FIG. 8B
FIG. 8C
FIG. 8D

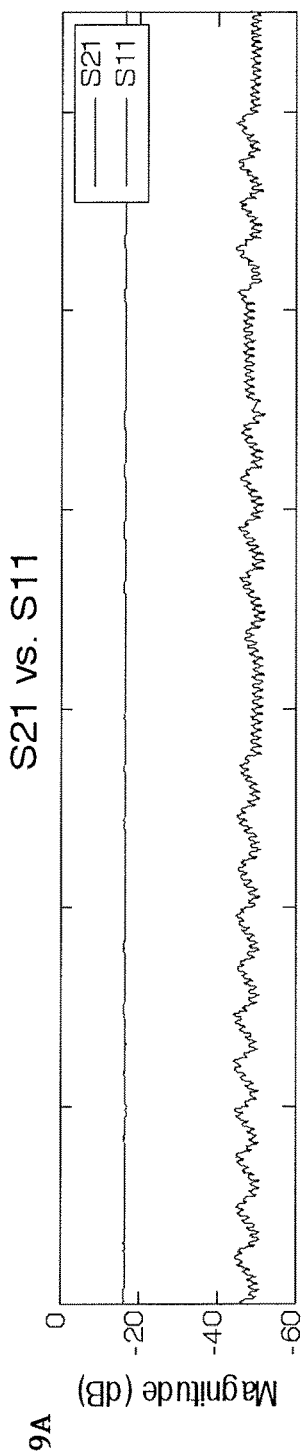
FIG. 9A
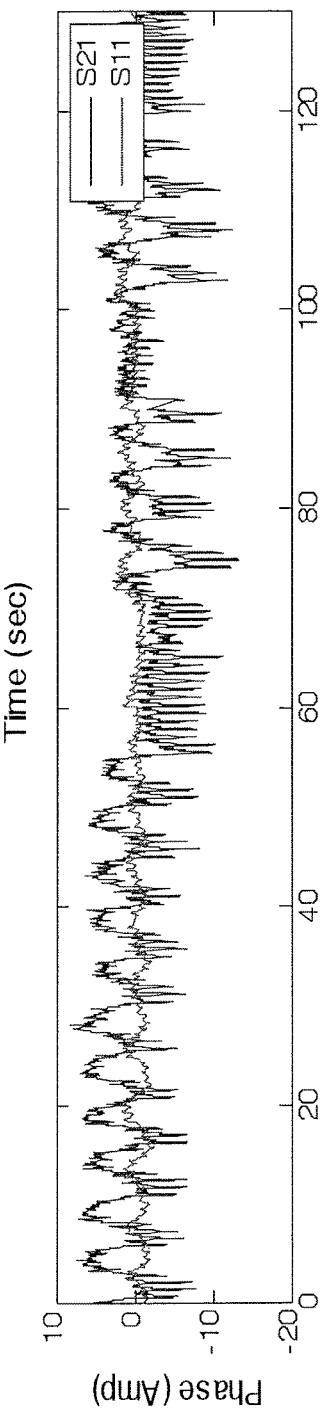
FIG. 9B
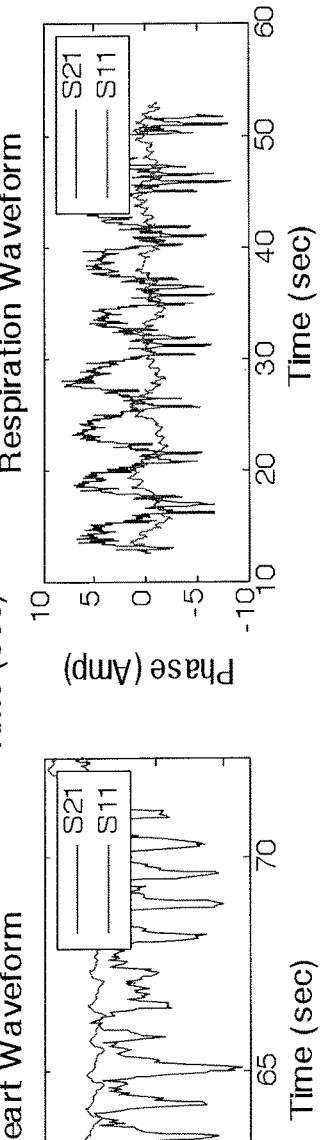
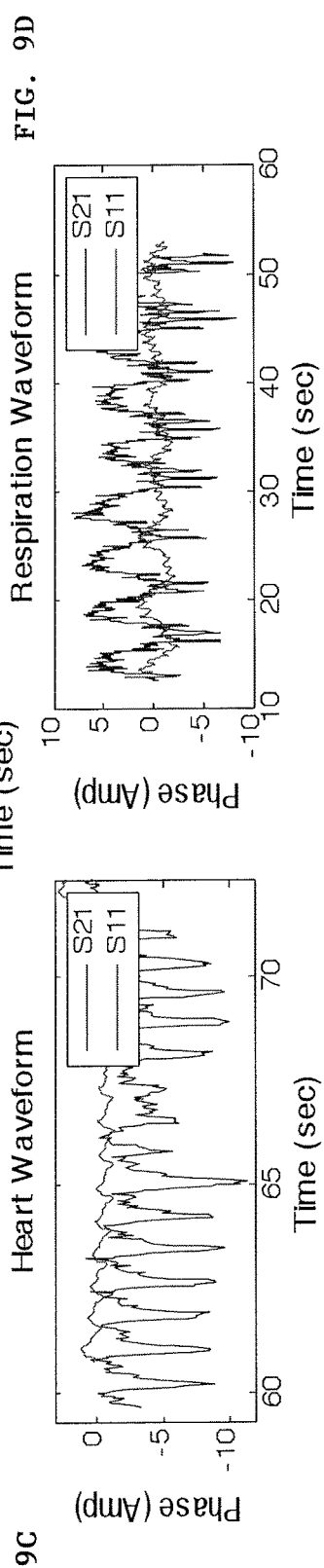
FIG. 9C
FIG. 9D

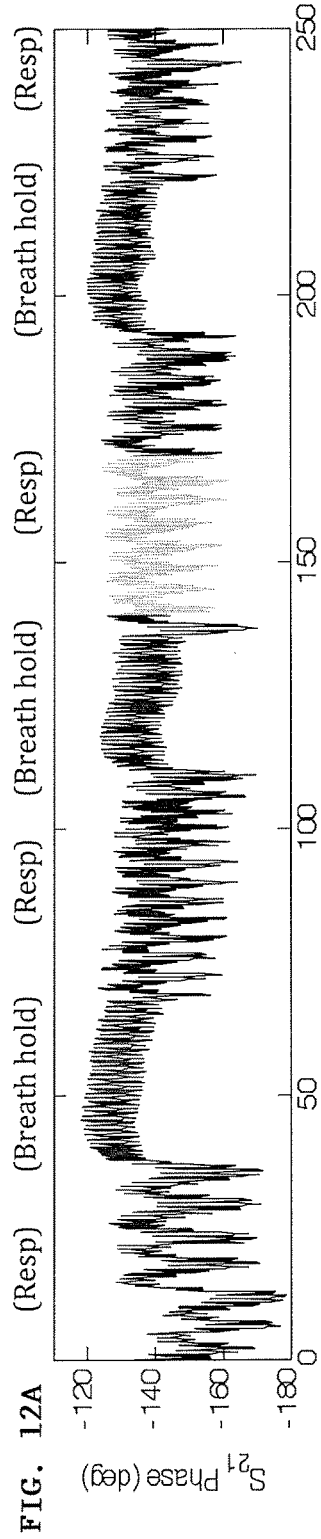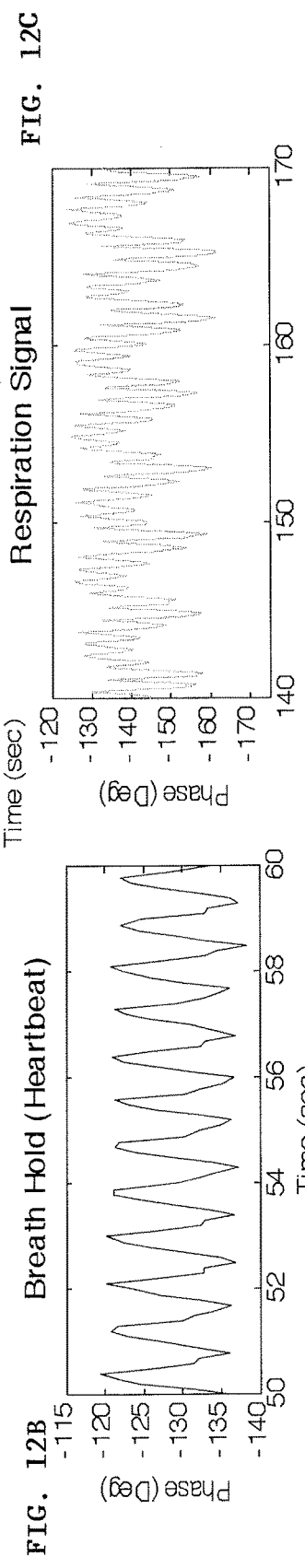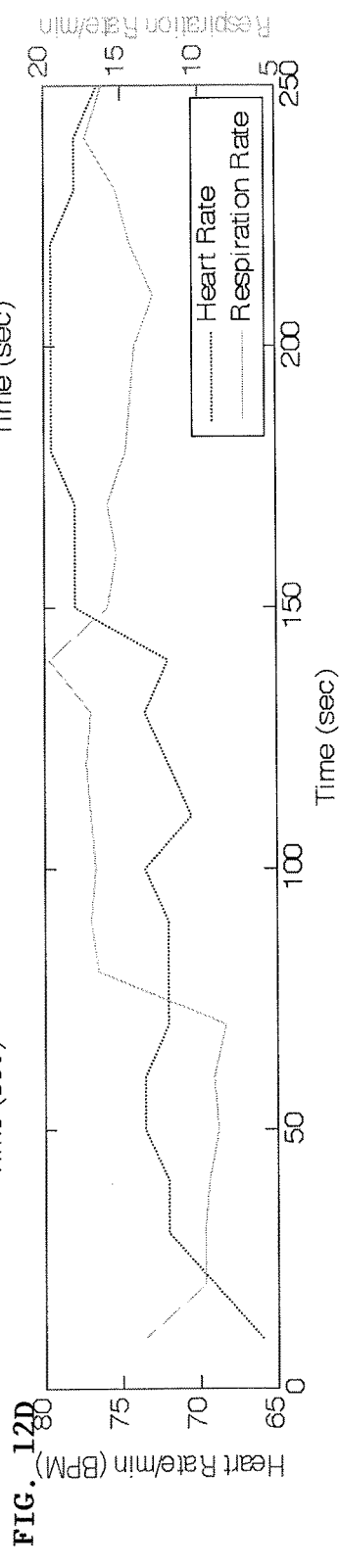
FIG. 12A
FIG. 12B
FIG. 12C
FIG. 12D

MICROWAVE STETHOSCOPE FOR MEASURING CARDIO-PULMONARY VITAL SIGNS AND LUNG WATER CONTENT

This U.S. patent application claims the priority filing dates of U.S. Provisional Application No. 61/816,632 filed on Apr. 26, 2013, and U.S. Provisional Application No. 61/932,958 filed on Jan. 29, 2014, of inventor(s) in common herewith, and are incorporated by reference herein.

The subject matter herein was developed in part under a grant provided by the U.S. Government, National Science Foundation, I-Corps Grant No. 001949-00001. The U.S. Government retains certain rights in the invention.

TECHNICAL FIELD

This U.S. patent application relates to a novel non-invasive microwave stethoscope employed as a vital signs sensor that can simultaneously measure and extract multiple vital signs parameters including the heart rate, respiration rate, heart waveform, and changes in lung water content from a single microwave measurement.

BACKGROUND OF INVENTION

Healthcare is, and remains, to be one of the most pressing challenges facing the U.S. and the world in the 21st century. A wide range of home-based continuous patient monitoring tools and applications integrated with intelligent and remote decision-making systems are proposed to remedy problems in the widespread delivery of healthcare.

For home-based continuous patient monitoring initiatives, technologies such as digital telecommunications, telemedicine, electronic medical records (EMR), wireless communications, artificial intelligence (AI) and novel medical sensors need to be employed. Although, some of these components such as wireless communications, EMR, and digital communications have been developed at a level that satisfies the requirements of the continuous monitoring applications, some of the key technologies such as the medical sensors still require significant development. Many currently in use medical sensors still require wired data connections, thus, hindering patient mobility, measure only one specific vital sign (VS), and, many are not suitable for continuous monitoring and may be susceptible to motion artifacts and hence not ideal for patient mobility.

There has been no reliable, non-invasive, low-cost, and easy-to-use medical sensor developed to measure a patient's vital signs (VS) as well as other clinically important parameters such as the changes in the lung water content (LWC). The LWC is a medically important parameter since it can be used to reliably detect pulmonary edema at an early stage, and as follow up for treatment in critical burn and heart surgery patients. To overcome these limitations, a microwave stethoscope has been proposed as an integrated, multi-purpose, low-cost, and non-invasive microwave sensor for making multiple VS measurements in addition to LWC from a single microwave measurement, as described by N. Celik, R. Gagarin, H. S. Youn, and M. F. Iskander, "A Non-Invasive microwave sensor and signal processing technique for continuous monitoring of vital signs," IEEE Antennas and Wireless Propagation Letters, vol. 10, pp. 286-289, February 2011; R. Gagarin, N. Celik, H. S. Youn, and M. F. Iskander, "Microwave Stethoscope: A New Method for Measuring Human Vital Signs," in 2011 APS-URSI International Conference, Spokane, Wash., July 2011; N. Celik, R. Gagarin, H. S. Youn, J. Baker, and M. F. Iskander, "On the development of a low-cost real-time remote patient monitoring system using a novel non-invasive microwave vital signs sensor," in IEEE ICWIT Conference, Honolulu, 2010.

The proposed microwave stethoscope was based on microwave reflection coefficient measurements on a patient's chest. The microwave sensor was previously used for LWC measurements using transmission coefficients across the thorax. Studies using animals and isolated lung experiments have validated the feasibility, sensitivity and accuracy of the transmission coefficient measurements in detecting the changes in LWC. It was observed that the measured transmission coefficient includes additional VS data such as heartbeat and respiration. To exploit this additional information, a multi-purpose sensor capable of measuring multiple VS through a single measurement was developed. An integrated system that includes the sensor and a novel digital signal processing (DSP) algorithm was used to extract multiple VS such as respiration rate (RR), respiration amplitude (RA), heart rate (HR), and the heart-beat amplitude (HA) in addition to LWC.

However, microwave measurements based on transmission coefficients have required two properly aligned microwave sensors placed front-to-back across the thorax. High signal attenuation (low SNR) as the signal has to transmit/travel through the entire thorax, reflect and attenuate through many layers of tissue. This made the transmission measurement procedure unusable for large size people, and in some cases an excessive amount of electromagnetic energy (unsafe) was required. Pulsed signal systems were proposed but complicated the systems design and associated DSP algorithms. Maintaining front-to-back sensor alignment also presented problems. In some animal experiments, x-ray images were employed for alignment of the transmission and receiver sensors. The front-to-back transmission approach thus limited the implementation and practical use of microwave measurement technology.

Microwave measurements based on use of a single sensor placed on a patient's chest for transmission and reception of reflection signals were found to provide insufficient signal information. The reflection measurement approach was found to be very insensitive to changes in lung water content and heart related changes vital signs. Reflection signals are dominated by reflection at the surface tissue layers and hence lack sensitivity to desired monitoring of vital signs and changes in lung water content.

SUMMARY OF INVENTION

It is therefore a principal object of the present invention to provide a microwave stethoscope measurement method and device configuration that can measure a patient's vital signs (VS) as well as other clinically important parameters such as changes in lung water content (LWC). It is a specific object of the invention to provide a microwave stethoscope that avoids the problems of difficulty of use in transmission measurement methods and insufficient signal information of reflection measurement methods.

In accordance with the present invention, a microwave stethoscope measurement method and sensor apparatus employ a microwave transmission sensor and a microwave reception sensor placed on a patient's chest in spaced-apart side-by-side configuration for monitoring patient vital signs and lung water content and other critical measurements.

In a preferred embodiment, the transmission sensor has a coplanar waveguide structure with a conductive ground plane and a center microline strip in a central aperture of the ground plane that is carried on a substrate. The reception sensor may be of the same design as the transmission sensor. The side-by-side sensors are spaced apart a separation distance of about 1-3 cm between sensors and are spaced apart in lateral chest orientation. A preferred placement location is over the bottom portion of the left lung of a patient near the bottom left of the sternum between left ribs 6 and 7. A preferred frequency range for the microwave signal is from about 700 MHz to 1.5 GHz, with an optimal range in the FCC allocated frequencies of 915 MHz and 920 MHz for medical and industrial applications (ISM band). It is found advantageous to use broadband sensors and multi-frequency measurements to better identify and possibly separate the various signals as the signal coefficients can be measured simultaneously at multiple frequencies and enables monitoring of a patient's body at various penetration depths and eliciting maximum medical information.

The side-by-side transmission-reception method combines the advantages of signal quality of front-to-back transmission as well as the simplicity of the reflection coefficient of a single reflection sensor. For optimum side-by-side transmission measurements, it is critically important that the sensors couple the electromagnetic (EM) energy effectively to the human body at the contact areas and with minimal leakage around the body.

Sensor design improvements also include textile fabrication of the sensor for wearer comfort and to improve contact with the patient's skin. In a preferred embodiment, a textile sensor is comprised of conductive steel thread embroidered with nylon thread on a felt fabric, and a coaxial cable is sewn to the back of the ground plane and the center transmission line through the felt using conductive thread. A cloth patch is sewn onto the back of the sensor to minimize twisting of the cable.

Improvements in digital signal processing (DSP) of microwave sensor measurements are also provided by modification to the previously employed short time Fourier Transform (STFT) spectrum windowed-averaged algorithm. After STFT spectrum windowed averaged extraction of respiration rate (RR) and lung water content (LWC) waveforms, RR, the residual signal is band-pass filtered to isolate the heartbeat waveform, then a threshold-based peak detection algorithm is used that selects the highest peaks in each heartbeat and ignores smaller ones, and the heart rate (HR) is calculated by counting the number of peaks in given intervals. The microwave sensor measurements may thus be used for extraction of monitoring data on vital signs (VS) and other critical parameters such as lung water content (LWC), stroke volume (SV) and cardiac output.

Improvements in continuous or remote monitoring of patient VS, LWC, and other critical medical information are also provided by delivering microwave sensor output data for monitoring displays on mobile devices such as smartphones.

Other objects, features, and advantages of the present invention will be explained in the following detailed description of the invention having reference to the appended drawings.

BRIEF DESCRIPTION OF DRAWINGS

FIGS. 8A-8D show a comparison of experimental results of transmission coefficient measurements, for magnitude, phase, heart, and respiration, respectively, between sensors in front-to-back (FB) configuration and side-by-side (SS) configuration.

FIGS. 9A-9D show a comparison of experimental results of transmission coefficient measurements, for magnitude, phase, heart, and respiration, respectively, between sensors in reflection (single sensor) configuration and side-by-side (SS) configuration.

FIGS. 12A-12C show a comparison of experimental results of transmission coefficient measurements, for breathing, heartbeat, and respiration, respectively, for microwave measurement using the textile sensor design, and FIG. 12D shows calculated respiration and heart rates.

DETAILED DESCRIPTION OF INVENTION

Certain preferred embodiments and implementation examples of the present invention are described in detail below. However, it is to be understood that the are illustrative only, and that the principles of the invention disclosed herein are applicable to other related or equivalent modifications, variations, and fields of application.

Figure 1:
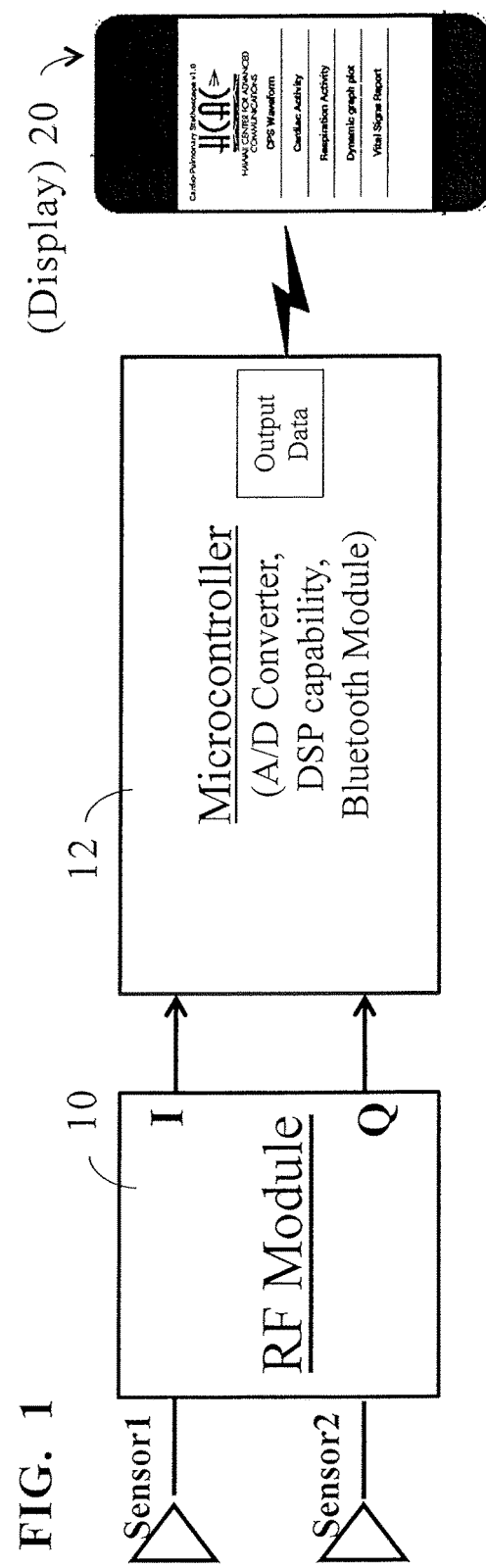
FIG. 1 is a schematic diagram illustrating a cardio-pulmonary (CP) microwave stethoscope measurement method and device configuration in accordance with the present invention.

Referring to FIG. 1, a schematic diagram illustrates a cardio-pulmonary (CP) microwave stethoscope measurement method and device configuration employing a paired sensor array comprised of a microwave transmission Sensor-1 and a microwave reception Sensor-2 placed on a patient's chest in spaced-apart side-by-side configuration for taking integrated vital signs (VS) and lung water content (LWC) and other critical measurements. A radio-frequency (RF) module 10 is used to send a microwave signal to the transmission Sensor-1 which transmits the signal through the skin and tissues of the thorax in position at a patient heart-lung location, and receives a returned microwave signal at the reception Sensor-2 which is returned to the RF module 10. The signal transmission and reception is controlled by a microcontroller 12 which may be incorporated with or in a separate unit from the RF module 10. The microcontroller 12 includes an analog-to-digital (ND) signal converter, and digital signal processing (DSP) capability for analyzing the returned microwave signal and converting it to vital signs (VS), lung water and other critical measurements. A wireless (e.g., Bluetooth) communication capability is provided to send output data by wireless transmission to a display 20. For remote and/or home-based patient monitoring, the display 20 may be a smartphone display operated by a client display application (smartphone app).

Figure 2:
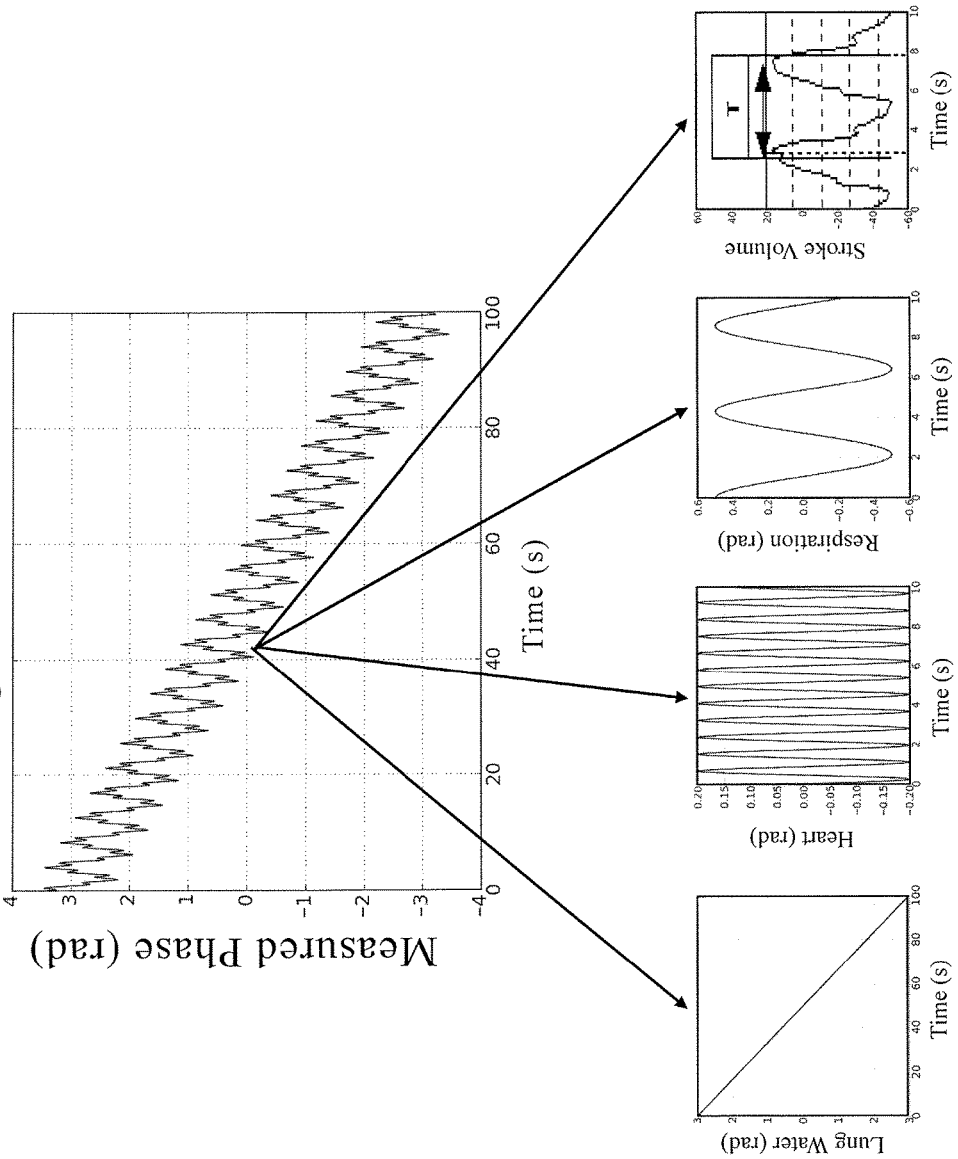
FIG. 2 illustrates conversion of the returned microwave measurement signal into various critical measurement displays provided by the system.

FIG. 2 illustrates conversion of the returned measurement signal into various critical measurement displays provided by the system, such as Lung Water (rad), Respiration (BrPM), Heartbeat (BPM), and Stroke Volume displays.

Figure 3:
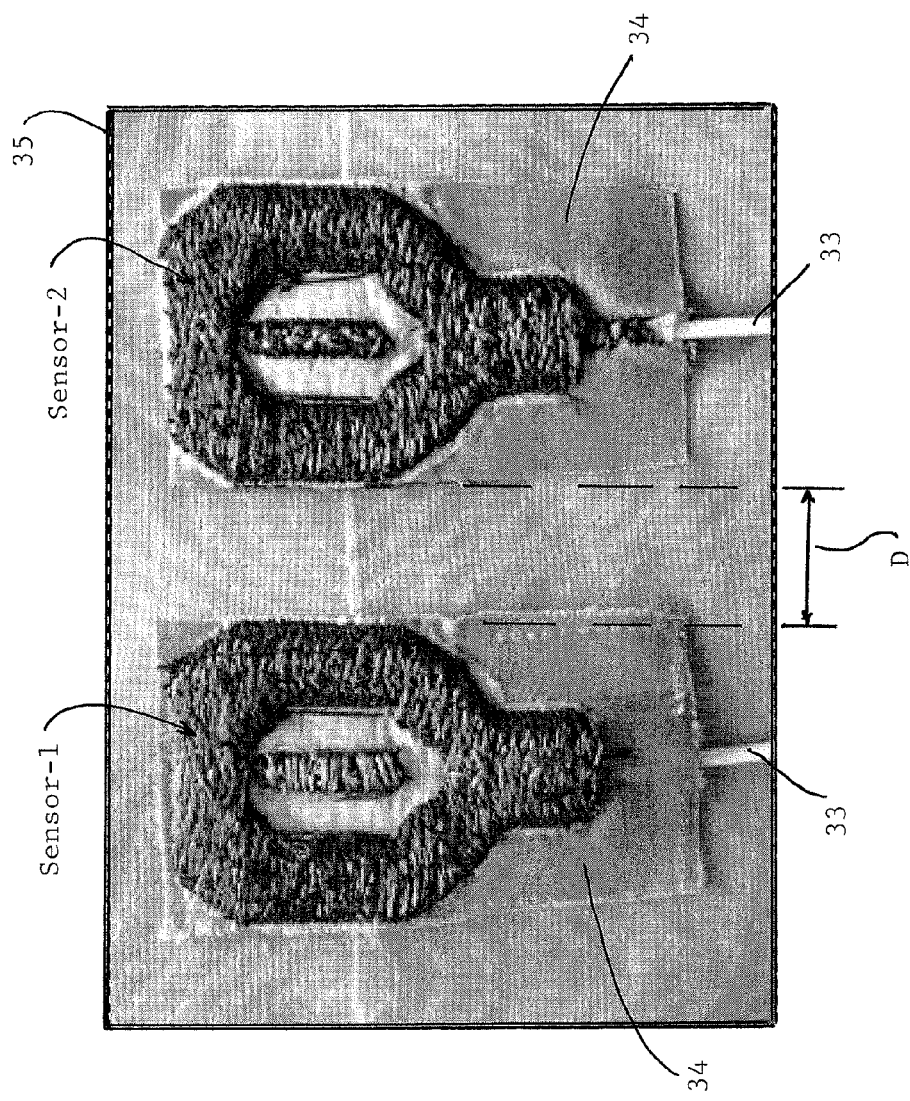
FIG. 3 shows the transmission Sensor-1 and reception Sensor-2 carried on a substrate in side-by-side configuration.

FIG. 3 shows a microwave transmission Sensor-1 and reception Sensor-2 embedded on patch substrates 34 in side-by-side configuration on a base layer 35 for mounting them on the skin on a patient's chest. A preferred design for the transmission Sensor-1 is a coplanar waveguide structure with a center microline strip in a central aperture that is carried on a substrate. The reception Sensor-2 may be of the same design as the transmission Sensor-1 or have a modified design. The two sensors are spaced apart by a spacing distance D, which is chosen to minimize electromagnetic (EM) coupling between the proximate conductive edges of the sensors and to maximize signal-to-noise ratio (SNR) of the returned signal. An optimum separation distance D for the preferred embodiments described herein is about 1-3 cm. Larger separations are found to result in weaker signals (low SNR) and closer separations result is a strong electromagnetic (EM) coupling between the sensors and reduces sensitivity to vital signs and changes in lung water content.

Figure 4:
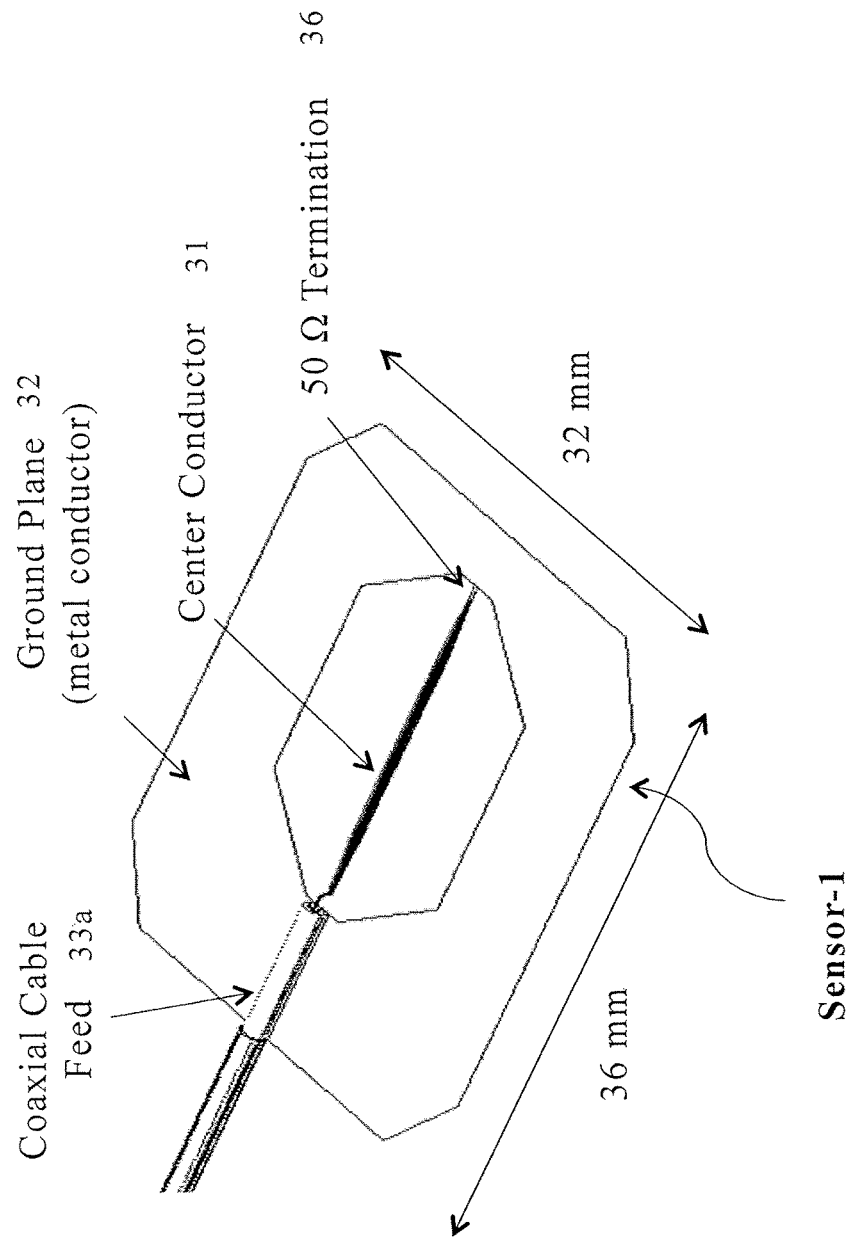
FIG. 4 shows a preferred example of the microwave transmission sensor with an adapter connector to a feeder coaxial cable.

FIG. 4 shows a preferred example for the transmission sensor having a coaxial cable feed 33a connected to a microstrip center conductor 31 positioned in a central aperture of and terminating in a resistive (e.g. 50 ohm) termination 36 in electrical contact with a metal conductor ground plane 32. The sensor is shown with length-width dimensions of 34 mm×32 mm for illustration.

Figure 5:
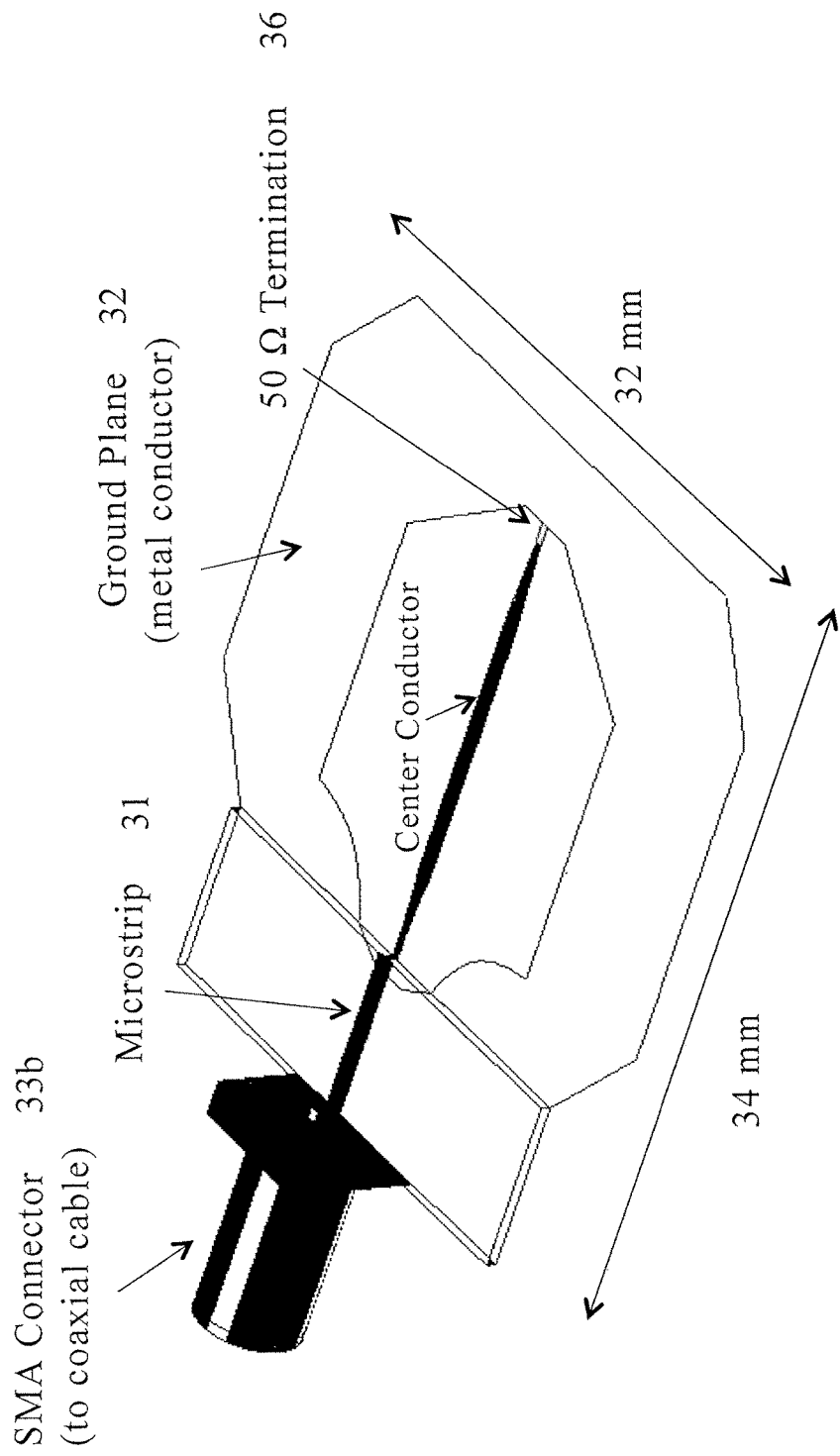
FIG. 5 shows an alternative structure for the microwave transmission sensor with a direct coaxial cable feeding structure.

FIG. 5 shows an alternative structure for the transmission sensor having an adapter (SMA) connector for a coaxial cable connection to the microstrip center conductor 31. The sensor is shown with length-width dimensions of 36 mm×32 mm for illustration.

Figure 6:
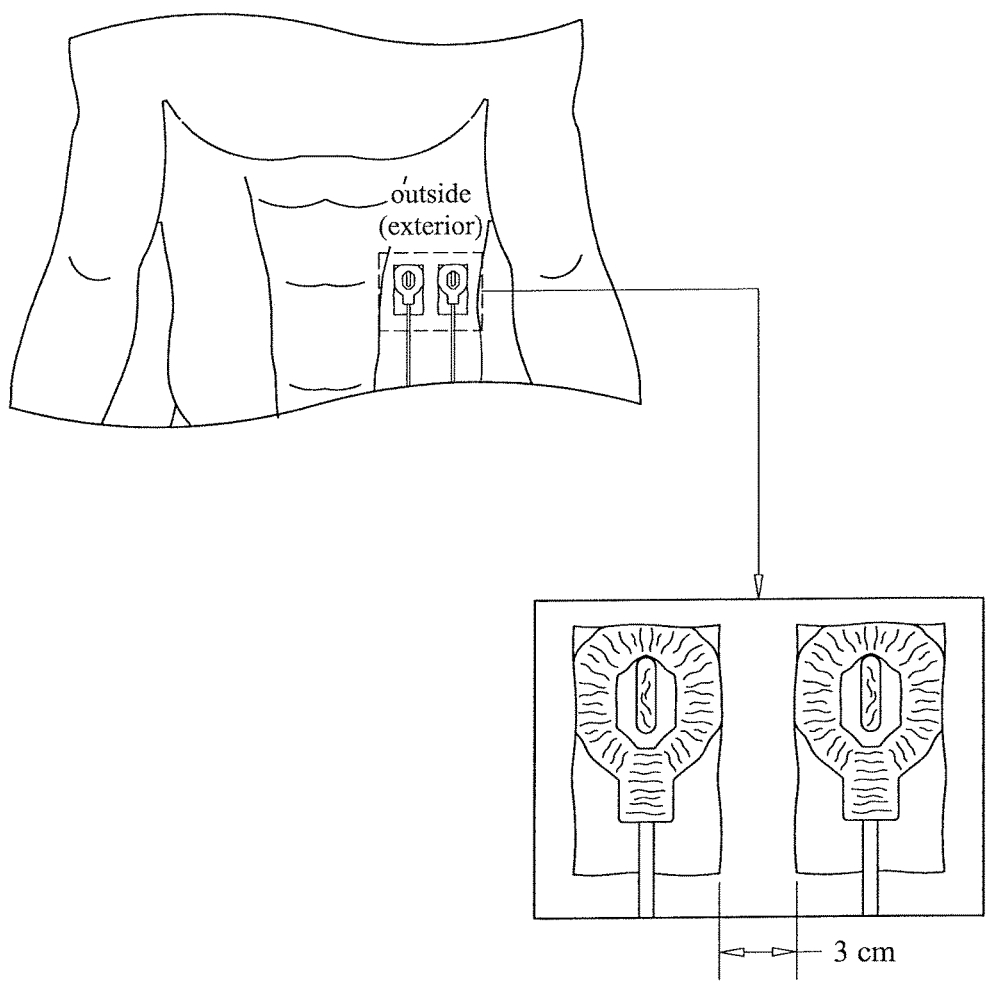
FIG. 6 shows the transmission and reception sensors mounted in side-by-side configuration in contact with the patient's chest.

FIG. 6 shows the transmission and reception sensors mounted in side-by-side configuration in contact with the patient's chest.

Side-By-Side Sensor Example

In a preferred example of the side-by-side sensor unit, the microwave transmission sensor has a coplanar waveguide structure that is fabricated on a flexible substrate. In determining an optimum operating frequency for the microwave transmission sensor, tradeoffs may be made between desired depth of penetration in the human body (low frequency) and sensitivity to phase changes (high frequency). A preferred frequency range is from 700 MHz to 1.5 GHz, with an optimal range in the FCC allocated frequencies of 915 MHz and 920 MHz for medical and industrial applications (ISM band). For integrated vital signs detection that includes surface (EKG) and subsurface (lung water and cardiac activity) measurements, it is advantageous to use broadband sensors and multi-frequency measurements to better identify and possibly separate the various signals. With broadband sensors, the signal coefficients can be measured simultaneously at multiple frequencies and enables monitoring of a patient's body at various penetration depths and eliciting maximum medical information.

Figure 7:
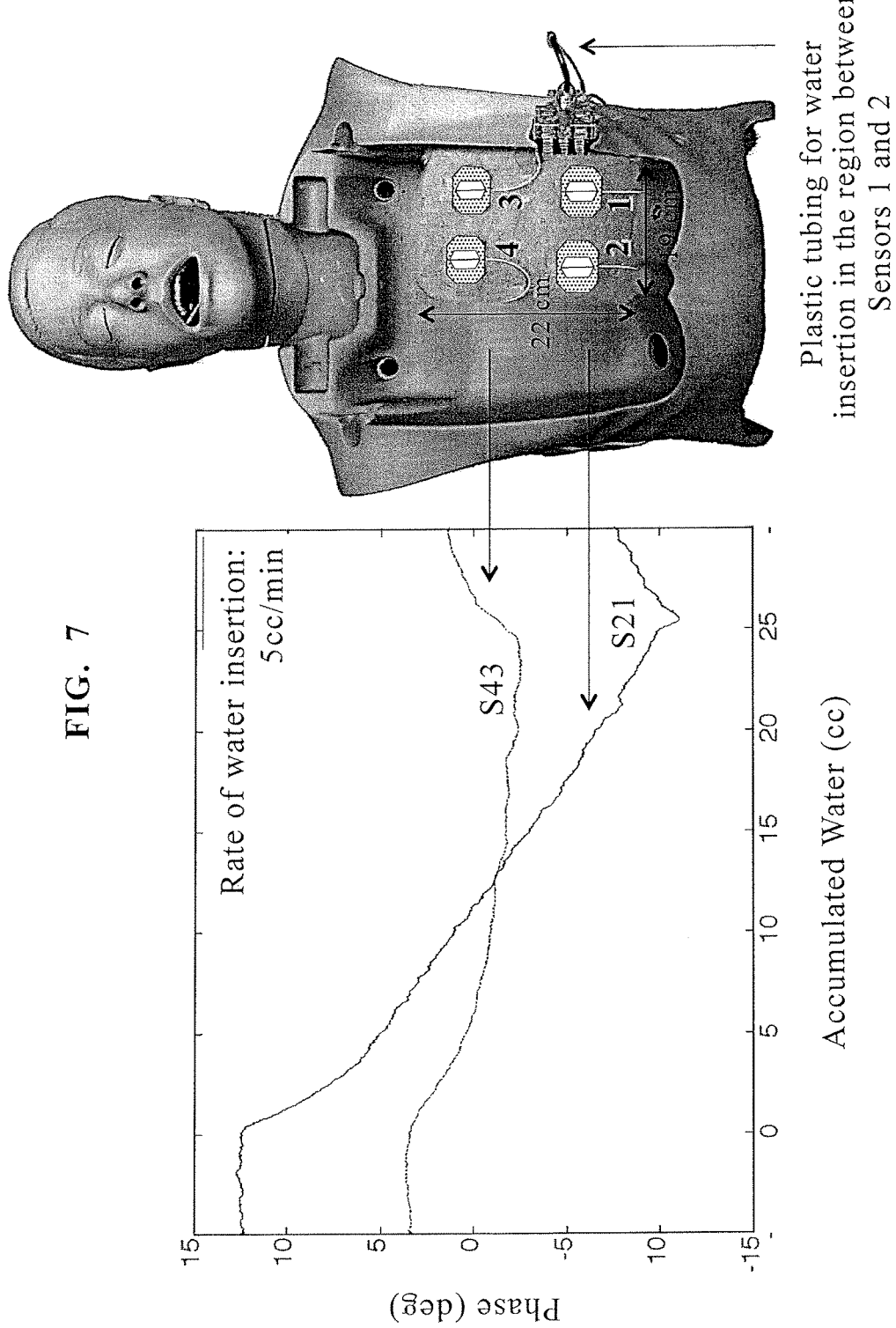
FIG. 7 shows simulation results of microwave sensitivity to changes in lung water content in lung tissue to predict lung water distribution.
Figure 10A:
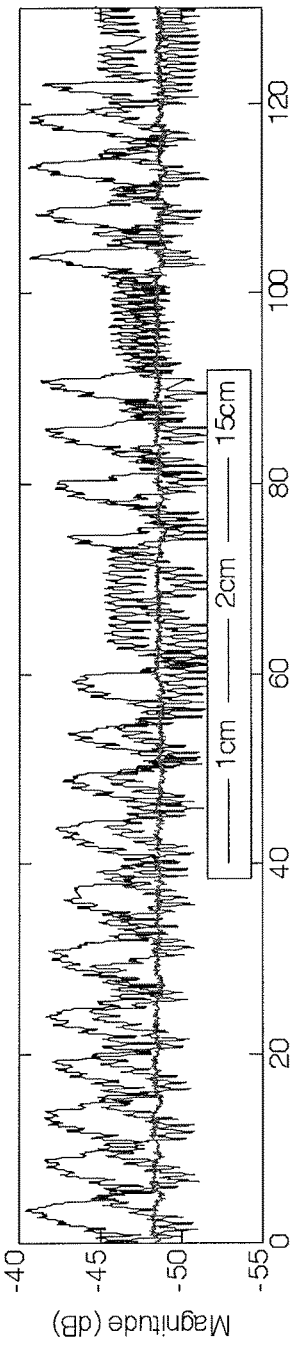
FIGS. 10A-10D show a comparison of experimental results of transmission coefficient measurements, for magnitude, phase, heart, and respiration, respectively, between sensors in side-by-side (SS) configuration with a distance between sensors of 1 cm, 2 cm, and 15 cm.
Figure 10B:
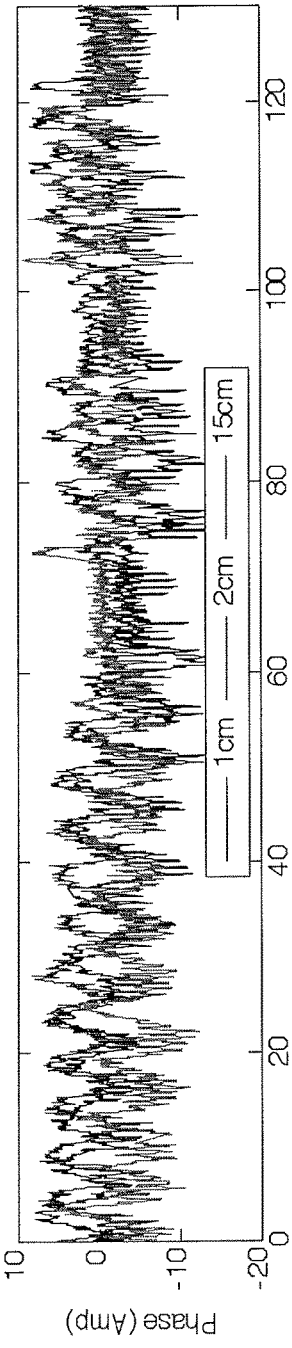
Figure 10D:
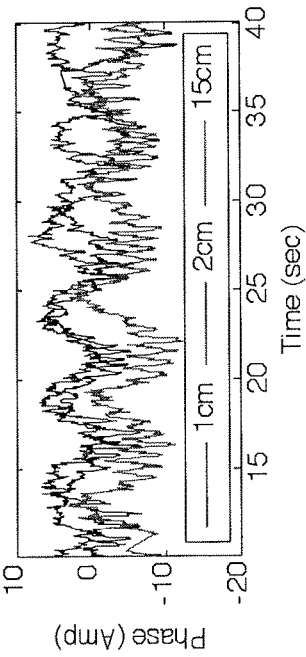
Figure 10C:
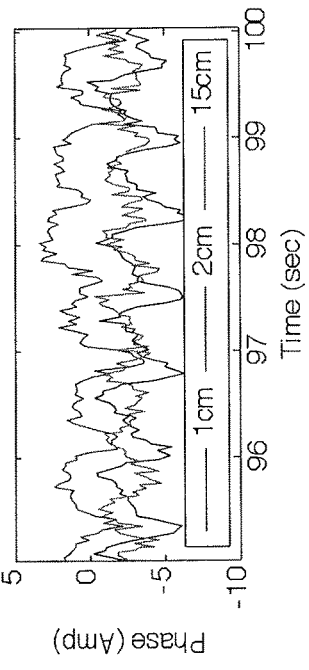

As illustrated in FIG. 7, simulation results from an anatomically realistic human body model indicated that microwave sensitivity to changes in lung water content in a specific region of lung tissue can help to predict lung water distribution. A first paired-sensor unit of Sensors 1 and 2 was positioned over a bottom portion of the model's left side lung, and a second paired-sensor unit of Sensors 3 and 4 was positioned over a top portion of the lung. Water was added (5 cc per minute, 25 cc total) into the bottom portion of the model's lung, while the top portion was kept constant (no increase). The graph in the figure shows transmission coefficient measurement (S21) on the bottom portion of the lung (from Sensor-1 and Sensor-2) having greater sensitivity to changes in the water content compared to the transmission coefficient measurement (S43) on the top portion of the lung (from Sensor-3 and Sensor-4). The simulation results showed a correlation between increasing amplitude in the phase of transmission coefficient between Sensors 1 and 2 and increasing fluid lower volume where lung water was increased by up to 25% over normal.

FIGS. 8A-8D show a comparison of experimental results of transmission coefficient measurements, for magnitude, phase, heart, and respiration, respectively, between sensors in front-to-back (FB) configuration and side-by-side configuration (with 1 cm sensor spacing). Transmission and reception microwave sensors in side-by-side configuration were placed over the bottom portion of the left lung of a patient near the bottom left of the sternum between left ribs 6 and 7. FIG. 8A shows that signal magnitude measured by the SS sensors (lighter line) tracked well compared to that measured by the FB sensors (darker line). The FB case had larger signal attenuation by about −20 dB. FIG. 8B shows that signal phase measured by the SS sensors also tracked well compared to the FB sensors. The FB case had less consistent fluctuations making it more difficult to extract vital signs and lung water content. The heart rate waveforms in FIG. 8C show that it was more difficult to identify signal from noise in the FB case, whereas the SS case was more consistent. The respiration rate waveforms in FIG. 8D show that the FB waveform had lower signal-to-noise ration (SNR) making it more difficult to identify waveform peaks in the FB waveform. SS transmission also avoids the need for sensor alignment in FB transmission, and requires lower input power while maintaining a better SNR since the SS signal does not need to go through the entire thorax.

FIGS. 9A-9D show a comparison of experimental results of transmission coefficient measurements, for magnitude, phase, heart, and respiration, respectively, between sensors in reflection (single sensor, S11 waveform) configuration and side-by-side (SS) configuration (S21 waveform). FIGS. 9A and 9B show that the S21 waveform in the SS case had greater phase amplitude (by 10-15 deg) compared to the S11 waveform in the reflection sensor case by less than 5 degrees. The S11 waveform was also more susceptible to noise by more than 5 degrees. FIG. 9C shows that the S21 case had a bigger amplitude (8-10 deg) of the Heart Waveform compared to the S11 case (1-2 deg). FIG. 9D shows that the S21 case had a bigger amplitude (10-15 deg) of the Respiration Waveform compared to the S11 case (3-5 deg). The results show that the S21 case would have greater sensitivity to vital signs such as heart rate, respiration rates, and to lung water content.

Compared to the side-by-side sensor configuration, the reflection coefficient measurement approach was found to be very insensitive to changes in lung water content and heart-related changes in vital signs. The reflected signal is dominated by reflection at the surface tissue layers and hence lack sensitivity to desired monitoring of vital signs and changes in lung water content. The side-by-side transmission method, therefore, combines advantages of both the front-to-back transmission approach (monitoring of changes in deep tissue layers) as well as the simplicity of the reflection coefficient approach (no need for critical alignment of sensors).

FIGS. 10A-10D show a comparison of experimental results of transmission coefficient measurements, for magnitude, phase, heart, and respiration, respectively, between sensors in side-by-side (SS) configuration with a distance between sensors of 1 cm, 2 cm, and 15 cm. The results overall showed a larger attenuation in signal (lower SNR) as the distance between the sensors increased. The 15 cm case had the largest attenuation at −48 dB, and the smallest phase amplitude (less than 10 deg). The 15 cm case also had the smallest phase amplitude of the heart waveform (4 deg) compared to the 1 cm and 2 cm cases (<6 deg). It was determined that placement of the sensors in parallel (lateral chest orientation) provides a maximum SNR, and a separation distance of about 1-3 cm provides best sensitivity. Larger separations result in weaker signals (low SNR) and closer separations result is strong EM coupling between the sensors and reduces sensitivity to vital signs and changes in lung water content.

The side-by-side sensor configuration can be further optimized with adjustments in electromagnetic energy coupler design, including good impedance match between the microwave feed and sensor, better energy distribution along the area of contact, insensitivity to human movement, and broadband characteristics.

Textile Sensor Design

In conjunction with the microwave measurement system, a novel textile sensor design is provided for greater convenience of use and wearability to the patient. The textile sensor design can be used for the above-described microwave sensor monitoring of vital signs (VS) such as respiration rate (RR), heart rate (HR), stroke volume (SV) and changes in lung water content (LWC). Experimental results comparing calculated values from the textile sensor design to a commercial VS monitoring device indicate that VS such as RR, HR and SV can be measured noninvasively, continuously and accurately using the textile sensor design.

Based on a study of various fabrication techniques for textile sensors and their durability, coupling efficiency and ability to minimize motion artifacts, it was found that embroidery of a fabric with conductive yarn (such as silverspun yarn) has the best structural stability due to its rigidity but still has sufficient flexibility to conform to irregular surfaces such as the human chest, which is critical for the coupling efficiency of the microwave sensor. In a preferred example, the design was further improved by replacing the conductive yarn with steel thread to increase the conductivity. Resistivity of the silverspun yarn was 10 $\Omega$/in, which conducted less EMF as compared to 1.3 $\Omega$/in (Makershed) for 2-ply steel thread.

A preferred fabrication process for the textile sensor will now be described. The preferred textile sensor is comprised of 2-ply conductive steel thread embroidered with nylon thread on a felt ($\epsilon_r$=1.3, tan $\delta$=0.02) fabric using a commercially available embroidery machine. It was embroidered with a 2 mm fill with 1 mm separation and 0° angle. In addition, coaxial cable, RG178, was sewn to the back of the ground plane and the center transmission line through the felt using the 2-ply conductive thread used for the embroidery. The center conductor of the cable is thin and prone to breaking at the junction between the cable and the center transmission line, so a cloth with adhesive patch was ironed and sewn onto the back of the sensor to minimize the twisting of the cable.

Figure 11A:
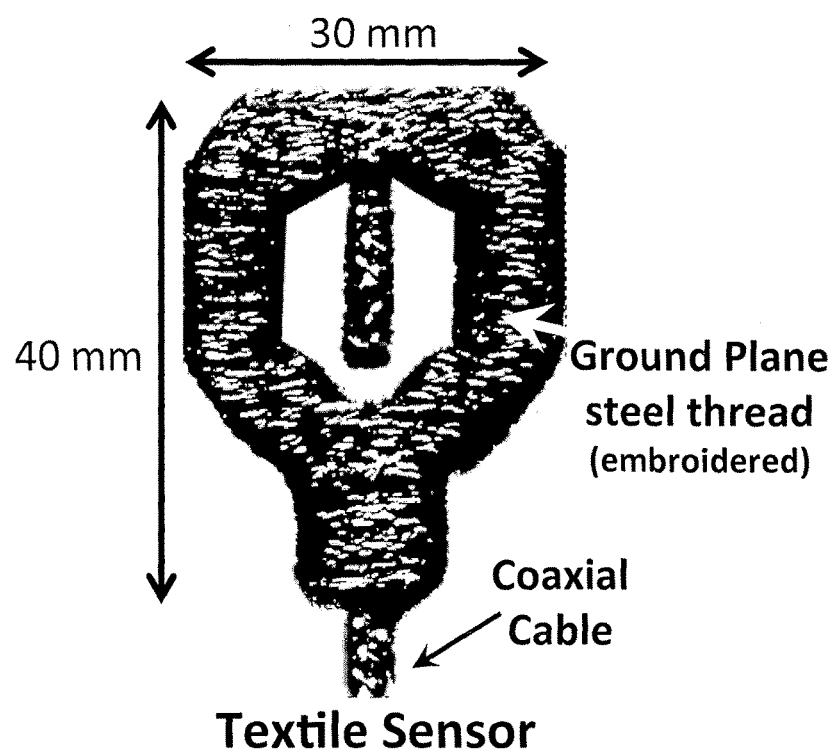
FIG. 11A shows a plan view and FIG. 11B shows in a cross-sectional view of a preferred design for a textile sensor for microwave sensor measurement.
Figure 11B:
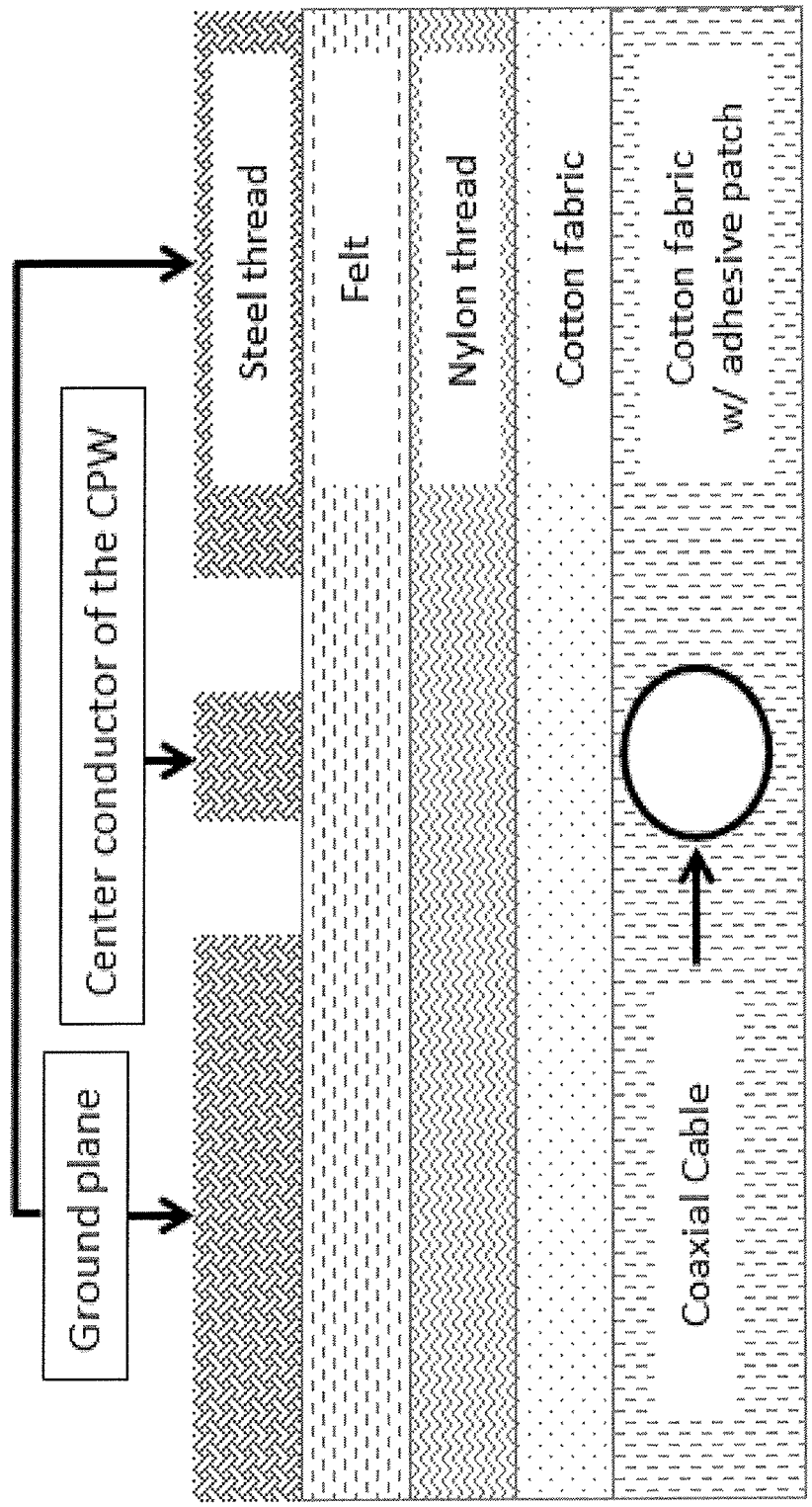

The fabricated textile sensor is shown in plan view FIG. 11A and in cross-sectional view in FIG. 11B. The sensor center conductor and ground plane are formed by steel thread embroidered on a felt, which is sewn by nylon thread to a cotton fabric base layer having a lower adhesive layer for mounting on the skin of the patient. A coaxial cable feed is sewn into the cotton fabric base layer and connected to the steel thread center conductor and ground plane.

A preferred placement location for the sensors in side-by-side configuration is over the bottom portion of the left lung of a patient near the bottom left of the sternum between left ribs 6 and 7. Stretchable fabric tape may be used to stabilize the contact of the sensors to the skin. The embroidered design results in the sensors being slightly raised from the fabric tape layer so as to maintain sufficient skin contact and therefore eliminating the need for conducting gel between the skin and the sensor.

Comparative tests were conducted using a control setup of commercial ECG leads (Propaq LT, Welch Allyn) and blood pressure handcuff (BPA-BTA, Vernier Software and Technologies) as benchmark devices for RR, HR and SV measurement, respectively. The experiment protocol consisted of series of normal breathing followed by breath holds. The experiments were conducted while the study participant was sitting on a chair. Phase and magnitude of the transmission and reflection coefficients were measured with a commercial network analyzer (Agilent PNA E8364B).

FIGS. 12A-12C show a comparison of experimental results of transmission coefficient measurements, for breathing, heartbeat, and respiration, respectively, for microwave measurement using the textile sensor design, and FIG. 12D shows calculated respiration and heart rates. The experimental results showed that VS measurements, such as RR, HR and SV, can be noninvasively measured using textile-based embroidered microwave sensors and indicated that the sensors were well coupled to the human body with minimal reflection of the microwave signal. Application of bandpass (BP) filtering and peak detection on the measured phase waveforms enabled accurate calculation of the vital signs. Measured values of the RR, HR and SV from the textile sensors were in close correlation to the values measured by the commercial Propaq LT ECG sensor and the mean arterial method from the blood pressure cuff. Measurements with the textile sensors also validated sensitivity to detecting accumulation LWC from a single microwave measurement.

Experimental tests were also conducted varying the body size of the patient (small, medium, large). The test results showed that the shapes of waveforms for all participants were similar and the DSP algorithm was able to extract and calculate the HR and RR with considerable accuracy despite the variation in sizes of patients. There were slight variations in the amplitude of the phase of the transmission coefficient for respiration and heartbeat waveforms between the small, medium and large size male. The textile sensor design was shown to be sensitive to vital signs and capable of accurately extracting heart rate and respiration rate.

For the side-by-side sensor configuration, it is critically important that the electromagnetic sensors couple the energy effectively to the human body, at the contact areas, and with very minimal leakage around the body. The electromagnetic energy coupler design can be optimized for key factors, including good impedance match between the feed and the sensor, better energy distribution along the area of contact, insensitivity to human movement, and broadband characteristics. Measurements with the textile sensor design compared favorably with existing commercially-available, FDA-approved devices. The textile fabrication of the sensor, and particularly embroidering conductive thread on the fabric support, provided good contact with the human body. The textile sensor can be incorporated into the chest area of wearable clothing, such as a T-shirt for males and a bra for females, for continuous and/or remote patient monitoring.

Digital Signal Processing of Microwave Sensor Waveforms

The extraction of multiple vital signs from a returned microwave coefficient measurement involves the problem of discriminating the fundamental frequencies from the harmonics. This is a task that can be realized by the recent advances in digital signal processing (DSP) technologies.

In earlier DSP vital signs (VS) extraction efforts, methods such as wavelet based signal decomposition approach, and short time Fourier Transform (STFT) based spectrum estimation approach have been employed, as described by R. Gagarin, H. S. Youn, N. Celik, and M. F. Iskander, "Non-invasive microwave technique for hemodynamic assessments," in 2010 APS-URSI International Conference, Toronto, Canada, Jul. 11-17, 2010; N. Celik, R. Gagarin, H. S. Youn, and M. F. Iskander, "A Non-Invasive microwave sensor and signal processing technique for continuous monitoring of vital signs," IEEE Antennas and Wireless Propagation Letters, vol. 10, pp. 286-289, February 2011; R. Gagarin, N. Celik, H. S. Youn, and M. F. Iskander, "Microwave Stethoscope: A New Method for Measuring Human Vital Signs," in 2011 APS-URSI International Conference, Spokane, Wash., July 2011. In the STFT based method, the stronger and slowly changing component due to the changes in lung water content (LWC) is estimated and removed using windowed linear regression after downsampling the signal at a sampling rate of 10 samples/sec. This downsampling operation increases the STFT accuracy in estimating the respiration rate (RR) which is at a fraction of a Hz. The piecewise linear plot obtained as a result of this regression is the estimated changes in the LWC. Then a windowed STFT operation is applied and the spectra corresponding to different windows are averaged to increase the SNR, as described by Madsen, A H, et al, "Signal processing methods for Doppler radar heart rate monitoring," in "Signal Processing Techniques for Knowledge Extraction and Information Fusion," D. Mandic, M. Golz, ed., Springer, 2008.

In the STFT windowed averaged spectrum, there are two major peaks corresponding to respiration rate (which is stronger) and heart rate (weaker). Through STFT and peak sorting, the stronger RR and RA are first estimated, then the weaker HR and HA are estimated by searching for the peaks in the 0.8-3 Hz frequency range. Depending on the window size and the number of windows averaged, increased sensitivity/accuracy can be obtained.

In pre-clinical human trials presently conducted, the measured heartbeat waveform included multiple peaks similar to an EKG like signal, depending on the location of the sensor on the chest. As a result, the HR extracted by the previously described STFT method becomes slightly off compared to the actual rates due to harmonics of the heartbeat signal. For the extraction of the correct HR, a modification in the DSP algorithm is implemented. After extracting the RR, and LWC using the linear regression and STFT, the residual signal is band-pass filtered (3 dB passband of 0.7 Hz to 5 Hz) to isolate the heartbeat waveform. Then, a threshold based peak detection algorithm is used that selects the highest peaks in each heartbeat and ignores smaller ones. To select the highest peaks, the ratio of each detected peak to the largest peak in a 10 second window is calculated and peaks that have a smaller ratio than the threshold value of 0.5 are omitted. The HR is calculated by counting the number of peaks in 10-second intervals.

Employing the side-by-side transmission sensor method and design, the DSP VS and LWC extraction results from pre-clinical human trials are illustrated in FIGS. 12A-12D.

The cardio-pulmonary microwave sensor can also be used to monitor patient cardiac conditions such as changes in stroke volume and cardiac output. Microwave phase signals can be processed by applying band pass filtering techniques and delineating peak and valley points of the microwave phase signals using a combination of techniques as described by N. Celik, et al., "A Non-Invasive Microwave Sensor and Signal Processing Technique for Continuous Monitoring of Vital Signs," IEEE, February 2011, Antennas and Wireless Propagation Letters, Vol. 10, pp. 286-289; B. N. Li, M. C. Dong and M. I. Vai, "On an automatic delineator for arterial blood pressure waveforms," Biomedical Signal Processing and Control, 2009; J. X. Sun, A. T. Reisner, M. Saeed and R. G. Mark, "Estimating cardiac output from arterial blood pressure waveforms, a critical evaluation using the MIMIC II database," Computers in Cardiology, vol. 32, pp. 295-298, 2005.

In a preprocessing step, a linear trend is subtracted from the phase data and the DC mean is removed from the signals. The waveform is normalized to the same scale as a comparative arterial blood pressure (ABP) waveform. A moving average filter of window length (such as 10) is applied to the signal to remove some high frequency components and for efficient detection of peak and valley points. Then fiducial points, such as peak and valley, are detected in the signal. The peak-to-peak distance or interval is equivalent to the respiration rate (RR) interval of EKG signals. The microwave sensor measurements were found to have significant correlation to arterial blood pressure waveforms. Changes in microwave sensor measurements were found to be proportional to the amount of blood pumped by the heart during each cycle or impulse, and therefore can be used to non-invasively measure cardiac parameters such as stroke volume and cardiac output.

Mobile (Smartphone) Monitoring Displays

Improvements in continuous or remote monitoring of patient VS, LWC, and other critical medical information are also provided by delivering microwave sensor output data for patient monitoring displays on mobile devices such as smartphones.

Figure 13:
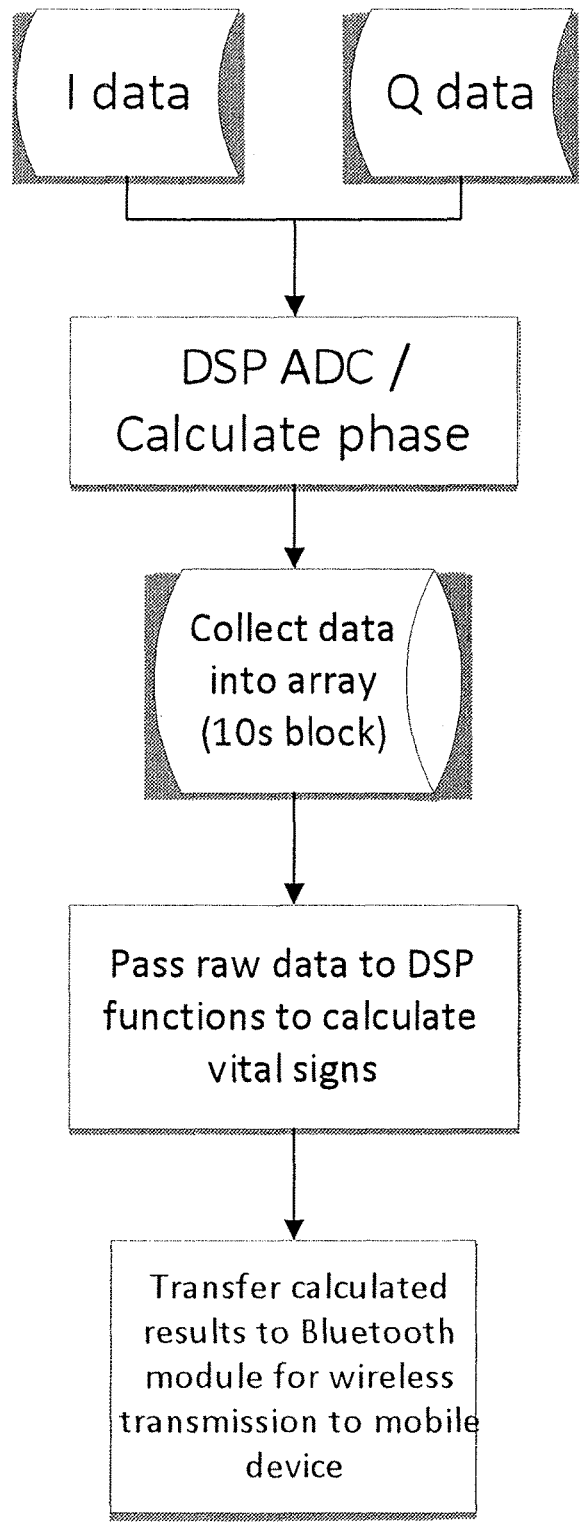
FIG. 13 shows a logic diagram for organizing CPS extracted medical information for display on a smartphone.

FIG. 13 shows a logic diagram for organizing CPS extracted medical information for display on a smartphone. In Step 130, the I data and Q data from the pair of sensors for side-by-side microwave transmission are collected. In Step 131, the analog format of the data is converted to digital format (ADC) for digital signal processing (DSP) such as described above. In Step 132, the converted digital data are collected into arrays such as the above-described blocks of 10 peak windows. In Step 133, the raw data are subjected to digital signal processing (DSP) such as described above to extract calculated measurements such as for vital signs (VS), lung water content (LWC), stroke volume, etc., as described above. In Step 134, the calculated VS, LWC, etc. results are transmitted wirelessly such as by Bluetooth protocol to a mobile device such as a smartphone for portable display of the results for patient monitoring. By extension, the results may also be transmitted wirelessly such as by wireless data protocol to a remote smartphone of a doctor or medical technician for remote patient monitoring.

In summary, the disclosed microwave stethoscope measurement method and sensor design configuration is capable of accurately monitoring a patient's vital signs (VS) as well as other clinically important parameters such as changes in lung water content (LWC). The microwave transmission sensor and reception sensor in spaced-apart side-by-side configuration combines the advantages of signal quality of front-to-back transmission as well as the simplicity of the reflection coefficient of a single reflection sensor. Sensor design improvements also include textile fabrication of the sensor for wearer comfort and to improve contact with the patient's skin. Improvements in digital signal processing (DSP) of microwave sensor measurements, by modification to the short time Fourier Transform (STFT) windowed-averaged algorithm, may be used for extraction of monitoring data on vital signs (VS) and other critical parameters such as lung water content (LWC), stroke volume (SV) and cardiac output. Improvements in continuous or remote monitoring of patient critical medical information are provided by delivering microwave sensor output data for monitoring displays on mobile devices such as smartphones.

It is to be understood that many modifications and variations may be devised given the above description of the principles of the invention. It is intended that all such modifications and variations be considered as within the spirit and scope of this invention, as defined in the following claims.

The invention claimed is:

1. A microwave stethoscope measurement apparatus comprising: a microwave transmission sensor and a microwave reception sensor in spaced-apart side-by-side configuration adapted to be placed on a patient's chest to over a selected heart-lung location in the body of the patient for monitoring lung water content and other vital signs of the patient, wherein the sensors are mounted on a single chest patch to be placed on the patient's chest, a microwave-frequency transmission/reception module coupled to said microwave transmission sensor to provide a microwave radiating signal from the patient's chest to the selected heart lung location in the patient's body from said microwave transmission sensor on the chest patch, and coupled to said microwave reception sensor to receive a microwave scattering signal returned from tissues at the selected heart-lung location in the patient's body to said microwave reception sensor on the chest patch, said returned microwave scattering signal being provided to said microwave-frequency transmission/reception module to be digitally analyzed for monitoring of lung water content; wherein the side-by-side microwave transmission and reception sensors are spaced apart a separation distance of 1-3 cm between sensors in lateral chest orientation on the chest patch in order to minimize attenuation of the returned microwave signal and/or electromagnetic coupling between the sensors so as to provide an optimal returned microwave signal for analysis of lung water content and other vital signs of the patient.

2. A microwave stethoscope measurement apparatus according to claim 1, wherein said microwave transmission sensor has a coplanar waveguide structure with a conductive ground plane and a center microline strip in a central aperture of the ground plane that is carried on a substrate.

3. A microwave stethoscope measurement apparatus according to claim 1, wherein said microwave transmission sensor is fed a transmitted microwave signal from said microwave-frequency transmission/reception module having a frequency range from about 700 MHz to 1.5 GHz.

4. A microwave stethoscope measurement apparatus according to claim 3, wherein the frequency range of the transmitted microwave signal fed from said microwave-frequency transmission/reception module is from about 915 MHz and 920 MHz allocated for medical and industrial applications (ISM band).

5. A microwave stethoscope measurement apparatus according to claim 1, wherein said microwave transmission sensor is a broadband sensor for multi-frequency measurements.

6. A microwave stethoscope measurement apparatus according to claim 1, wherein said microwave transmission sensor is fabricated as a textile sensor for wearer comfort and to improve contact with the patient's skin.

7. A microwave stethoscope measurement apparatus according to claim 6, wherein said textile sensor is comprised of conductive steel thread embroidered with nylon thread on a felt fabric.

8. A microwave stethoscope measurement apparatus according to claim 7, wherein the embroidered steel thread forms the conductive ground plane and center transmission line, and a coaxial cable is sewn in electrical contact with the back of the ground plane and the center transmission line through the felt.

9. A microwave stethoscope measurement apparatus according to claim 8, wherein said textile sensor is sewn to a cloth patch backing to minimize twisting of the coaxial cable.

10. A microwave stethoscope measurement apparatus according to claim 6, wherein said microwave reception sensor is formed of a similar design as the transmission sensor.

11. A microwave stethoscope measurement method comprising the steps of:

providing a microwave transmission sensor and a microwave reception sensor mounted on a single chest patch in spaced-apart side-by-side configuration to be placed on a patient's chest to over a selected heart-lung location in the body of the patient, wherein the side-by-side microwave transmission and reception sensors are spaced apart a separation distance between sensors in lateral chest orientation selected in order to minimize attenuation of the returned microwave signal and/or electromagnetic coupling between the sensors so as to provide an optimal returned microwave signal for analysis of lung water content and other vital signs of the patient, transmitting a microwave radiating signal via the microwave transmission sensor on the chest patch through the skin and into tissues at the selected heart-lung location in the patient's body and receiving a returned microwave scattering signal via the microwave reception sensor on the chest patch, applying digital signal processing of the returned microwave scattering signal for extracting output data indicative of lung water content of the patient's medical condition, displaying the output data on a display for monitoring the patient's medical condition.

12. A microwave stethoscope measurement method according to claim 11, wherein said applied digital signal processing also extracts output data indicative of the patient's vital signs, and other critical measurements.

13. A microwave stethoscope measurement method according to claim 11, wherein said applied digital signal processing also extracts output data indicative of the patient's stroke volume and/or cardiac output.

14. A microwave stethoscope measurement method according to claim 11, wherein the microwave transmission and reception sensors are placed on the patient's chest spaced apart a separation distance of about 1-3 cm between sensors in lateral chest orientation.

15. A microwave stethoscope measurement method according to claim 11, wherein said microwave transmission sensor is fed a microwave signal having a frequency range from about 700 MHz to 1.5 GHz.

16. A microwave stethoscope measurement method according to claim 15, wherein said frequency range is from about 915 MHz and 920 MHz allocated for medical and industrial applications (ISM band).

17. A microwave stethoscope measurement apparatus according to claim 11, wherein said microwave transmission sensor is a broadband sensor for multi-frequency measurements.

18. A microwave stethoscope measurement method according to claim 11, wherein said microwave transmission and reception sensors are fabricated with a textile fabric for wearer comfort and to improve contact with the patient's skin.

19. A microwave stethoscope measurement method according to claim 11, wherein said applied digital signal processing step comprises:

employing a short time Fourier Transform (STFT) spectrum windowed-averaged algorithm for extraction of waveforms for respiration rate (RR) and lung water content (LWC), comparing the lung water content (LWC) waveform from the returned microwave signal to the transmitted microwave signal in order to extract a change of phase and magnitude of phase change indicative of LWC measurement and change in LWC measurement, and band-pass filtering the extracted waveforms to isolate a heartbeat waveform, then applying a threshold-based peak detection algorithm to select highest peaks in each heartbeat and ignores smaller ones, and calculating a heart rate (HR) by counting the number of peaks in a given interval.

20. A microwave stethoscope measurement method according to claim 11, wherein said output data is transmitted wirelessly to a mobile digital communication device for remote monitoring of a patient's medical condition.

* * * * *